(12) United States Patent
Robinson

(10) Patent No.: US 10,093,886 B2
(45) Date of Patent: Oct. 9, 2018

(54) MULTI-PURPOSE CLEANER

(71) Applicant: Gregory E. Robinson, Tonawanda, NY (US)

(72) Inventor: Gregory E. Robinson, Tonawanda, NY (US)

( * ) Notice: Subject to any disclaimer, the term of this patent is extended or adjusted under 35 U.S.C. 154(b) by 0 days.

(21) Appl. No.: 15/439,577

(22) Filed: Feb. 22, 2017

(65) Prior Publication Data

US 2017/0158989 A1 Jun. 8, 2017

Related U.S. Application Data

(63) Continuation of application No. 14/619,932, filed on Feb. 11, 2015, now Pat. No. 9,611,449.

(51) Int. Cl.

| C11D 1/88 | (2006.01) |
|---|---|
| C11D 1/75 | (2006.01) |
| C11D 3/30 | (2006.01) |
| C11D 3/33 | (2006.01) |
| C11D 3/12 | (2006.01) |
| C11D 1/62 | (2006.01) |
| C11D 3/08 | (2006.01) |
| C11D 1/94 | (2006.01) |

(52) U.S. Cl.
CPC ............. *C11D 3/30* (2013.01); *C11D 1/62* (2013.01); *C11D 1/75* (2013.01); *C11D 1/88* (2013.01); *C11D 1/94* (2013.01); *C11D 3/08* (2013.01); *C11D 3/1246* (2013.01); *C11D 3/33* (2013.01)

(58) Field of Classification Search
CPC .... C11D 1/62; C11D 1/75; C11D 1/88; C11D 1/94; C11D 3/08; C11D 3/30; C11D 3/33
USPC ........ 510/237, 238, 433, 499, 503, 504, 511
See application file for complete search history.

(56) References Cited

U.S. PATENT DOCUMENTS

| 5,348,679 | A * | 9/1994 | Weinhold | ................. | C11D 1/10 510/108 |
| 6,824,623 | B1 | 11/2004 | Gross et al. | | |
| 6,881,711 | B1 * | 4/2005 | Gershun | ................. | C11D 3/044 510/179 |
| 6,982,244 | B2 | 1/2006 | Gross | | |
| 7,018,969 | B1 | 3/2006 | Gross et al. | | |
| 7,309,684 | B2 | 12/2007 | Filippini et al. | | |
| 7,745,383 | B2 * | 6/2010 | Dreja | ................. | C11D 3/124 510/163 |
| 7,939,487 | B2 | 5/2011 | Scheuing et al. | | |
| 8,329,630 | B2 * | 12/2012 | Finison | ................. | C11D 3/0057 510/197 |
| 2002/0039988 | A1 * | 4/2002 | Kasturi | ................. | C11D 11/0023 510/461 |
| 2003/0139315 | A1 * | 7/2003 | Man | ................. | C11D 1/06 510/365 |
| 2005/0239674 | A1 * | 10/2005 | Dreja | ................. | C11D 3/124 510/180 |
| 2008/0041418 | A1 * | 2/2008 | Yagi | ................. | C11D 3/0036 134/6 |
| 2009/0165228 | A1 * | 7/2009 | Kilkenny | ................. | A01N 37/36 15/104.94 |
| 2010/0160201 | A1 * | 6/2010 | Scheuing | ................. | C11D 1/83 510/180 |
| 2010/0240563 | A1 * | 9/2010 | Jaynes | ................. | C08F 220/56 510/180 |
| 2011/0009309 | A1 * | 1/2011 | Mertens | ................. | C11D 3/3776 510/400 |
| 2011/0146725 | A1 * | 6/2011 | Woo | ................. | A61L 9/01 134/26 |
| 2012/0021963 | A1 * | 1/2012 | Kneipp | ................. | C23G 1/24 510/259 |
| 2012/0156377 | A1 * | 6/2012 | Veith | ................. | C11D 3/3707 427/331 |
| 2012/0165240 | A1 * | 6/2012 | Finison | ................. | C11D 3/0057 510/365 |
| 2012/0213759 | A1 * | 8/2012 | Karsten | ................. | C11D 1/62 424/94.1 |
| 2013/0210695 | A1 * | 8/2013 | Bjelopavlic | ................. | C11D 1/66 510/470 |
| 2013/0255729 | A1 * | 10/2013 | Hodge | ................. | B08B 3/02 134/34 |
| 2014/0148372 | A1 * | 5/2014 | Man | ................. | C11D 1/75 510/407 |
| 2015/0240188 | A1 * | 8/2015 | Morigaki | ................. | C11D 1/16 510/426 |
| 2016/0319221 | A1 * | 11/2016 | Man | ................. | C11D 1/75 |
| 2017/0183606 | A1 * | 6/2017 | Hodge | ................. | C11D 1/8255 |
| 2017/0233680 | A1 * | 8/2017 | Hodge | ................. | C11D 1/8255 510/365 |

OTHER PUBLICATIONS

Tomamine Ether Amines—Product Guide, Air Products, p. 1-11, Mar. 2012.*
Tomamine Amphoteric L Surfactant, Air Products, p. 1-2, 2011.*
Air Products, Material Safety Data Sheet, Tomamine Amphoteric L Surfactant, p. 1-7, Dec. 2007.*

* cited by examiner

*Primary Examiner* — Gregory R Delcotto
(74) *Attorney, Agent, or Firm* — Vincent G LoTempio; Kloss, Stenger & LoTempio; David T. Stephenson

(57) ABSTRACT

Provided is a multi-function liquid cleaning composition. The cleaning composition may be diluted to produce a composition for a variety of different purposes. The cleaning solution is particularly effective as a degreaser for heavy grease removal. Heavy grease includes the type that may accumulate on motor vehicles. The cleaning formulation is environmentally benign and non-toxic.

10 Claims, No Drawings

MULTI-PURPOSE CLEANER

This application is a continuation of U.S. patent application Ser. No. 14/619,932 with a filing date of Feb. 11, 2015.

FIELD OF THE INVENTION

The present disclosure relates to a multi-purpose liquid cleaning composition. The cleaner is particularly effective as a degreaser for use on heavy grease, including the type that may accumulate on motor vehicles. The cleaning composition is non-toxic, biodegradable, and will not cause harm to the user, the surface, or the environment.

BACKGROUND OF THE INVENTION

The present disclosure relates to an environmentally benign, yet powerful, cleaning composition. Commercially available cleaning compositions generally incorporate chemicals that are detrimental to the environment. These chemicals include surfactants, solvents, boosters and chelators. Other common ingredients in cleaning compositions that can harm the environment include phosphates, nitrilotriacetic acid, ethylenediaminetetraacetic acid, nonylphenol ethoxylates, and heavy metals; some of which have been demonstrated to accumulate in ground water.

Toxic chemicals from cleaning compositions have been found in fresh water such as ponds, lakes, and streams in high levels. Aquatic organisms, including both plants and animals, are at risk from exposure to high levels of these chemicals in water systems. Further, humans exposed to these chemicals through water systems may suffer from health problems. Additionally, many cleaning compositions contain toxic or carcinogenic chemicals, including volatile organic compounds (VOCs) and hazardous air pollutants (HAPs) that can pollute the air. As a result, alternative cleaning compositions which do not contain these and other environmental and bio-hazardous chemicals are desired.

Typical cleaning compositions require multiple surfactants, solvents, and builder combinations to achieve adequate consumer performance. For cost-effectiveness and out of concern for the environment, focus has shifted to producing cleaning compositions containing naturally occurring chemicals. There has long been a need for a naturally-based cleaning composition that achieves acceptable consumer performance with a limited number of natural components compared to highly developed compositions using synthetic surfactants and solvents.

A number of representative compositions include high numbers of ingredients and synthetic compounds, leading to higher costs of production and limited usefulness. For example, U.S. Pat. Nos. 6,759,382, 6,686,323 6,117,820 and 6,537,960 disclose cleaning compositions with high complexity and large numbers of ingredients.

Prior compositions have not successfully minimized ingredients while maintaining quality of cleaning, particularly with environmentally benign compounds. Accordingly, it is an object of the present invention to provide a cleaning composition that overcomes the disadvantages and shortcomings associated with existing cleaning compositions.

SUMMARY OF THE INVENTION

This composition is multi-purpose cleaner, particularly effective for heavy grease removal. Heavy grease includes the type that may accumulate on the sides or backs of diesel powered public transit buses and locomotives, subway cars, intercity trains and light rail vehicles. This composition may be customized for different purposes by adjusting the pH through dilution. Varying the levels of dilution of this composition results in a different pH targeted for specific applications.

In accordance with the above objects and those that will be mentioned and will become apparent below, one embodiment of the present invention comprises a natural cleaning composition having a chelating agent, which may be of the aminocarboxylate class of chelating agents. The formulation also contains a surfactant of the ethanolamine class. Additionally, the formulation contains an abrasive, such as sodium silicate. Further, the formulation includes an amphoteric surfactant such as b-Alanine,N-(2-carboxyethyl)-N-[3-(decyloxy)propyl]-, sodium salt (1:1). A thickener amine oxide such as ethanol, 2,2-iminobis-, N-(3-(branched decyloxy)propyl) derivs, N-oxides is also included. Finally, a quaternary amine surfactant such as Tomamine® Q-17-2 is included in this embodiment of the formulation of the present disclosure.

The formulations of the present disclosure may further comprise a chelating agent. A shine polymer may further be added for those applications requiring a shined surface following cleaning. Optional compositions further contain dyes and/or fragrances.

DETAILED DESCRIPTION

This disclosure provides formulations for environmentally friendly specialty cleaning chemicals. The present disclosure provides three separate environmentally friendly cleaning formulations.

Method of Application

The cleaning composition of the present disclosure may be applied to the target surface by a variety of means, including direct application by means of a spray, pump or aerosol dispensing means, or by other means, including the use of a carrier, or dilution system, as for example, but not limited to a wash, dip or immersion process. Regarding applications by use of a carrier, such suitable carriers include, for example, an impregnated wipe, foam, sponge, cloth, towel, tissue or paper towel or similar releasably absorbent carrier that enables the inventive compositions to be applied by direct physical contact and transferred from the carrier to the target surface, generally during a spreading, padding, rubbing or wiping operation. Combinations of a direct application, followed by a spreading, padding, rubbing or wiping operation performed with the aid of a foam, sponge, cloth, towel, tissue or paper towel, squeegee or similar wiping implement is also suitable for applying the cleaning compositions of the present disclosure.

The cleaning composition may be also be sprayed directly onto the target surface and therefore are typically packaged in a spray dispenser. The spray dispenser can be any of the manually activated means for producing a spray of liquid droplets as is known in the art, e.g., trigger-type, pump-type, electrical spray, hydraulic nozzle, sonic nebulizer, high pressure fog nozzle, non-aerosol self-pressurized, and aerosol-type spray means. Automatic activated means can also be used herein. These types of automatic means are similar to manually activated means with the exception that the propellant is replaced by a compressor. The spray dispenser can be an aerosol dispenser. Said aerosol dispenser comprises a container which can be constructed of any of the conventional materials employed in fabricating aerosol containers. A more complete description of commercially available aerosol-spray dispensers appears in U.S. Pat. Nos.

3,436,772 and 3,600,325, both of which are fully incorporated herein by reference. Alternatively, the spray dispenser can be a self-pressurized non-aerosol container having a convoluted liner and an elastomeric sleeve. A more complete description of self-pressurized spray dispensers can be found in U.S. Pat. Nos. 4,260,110; 5,111,971 and 5,232,126, both of which are fully incorporated herein by reference. The container and the pump mechanism can be constructed of any conventional material employed in fabricating pump-spray dispensers, including, but not limited to: polyethylene; polypropylene; polyethyleneterephthalate; blends of polyethylene, vinyl acetate, and rubber elastomer. Other materials can include stainless steel. A more complete disclosure of commercially available dispensing devices appears in: U.S. Pat. Nos. 4,082,223; 4,161,288; 4,274,560; 4,434,917; 4,735,347; 4,819,835; 4,895,279; and 5,303,867; all of which are fully incorporated herein by reference.

One of skill in the art would understand the term "about" is used herein to mean that a concentration of "about" a recited percentage (%) produces the desired degree of effectiveness in the compositions and methods of the present invention. One of skill in the art would further understand that the metes and bounds of "about" with respect to the concentration of any component in an embodiment can be determined by varying the concentration of one or more components (all percentages listed herein are by weight, as would be understood by one of ordinary skill in the art), determining the effectiveness of the mixture for each concentration, and determining the range of concentrations that produce mixtures with the desired degree of effectiveness in accordance with the present disclosure. The term "about" is further used to reflect the possibility that a mixture may contain trace components of other materials that do not alter the effectiveness or safety of the mixture.

It will be understood that emollients, humectants, fragrances, coloring agents, and other components may be added to or used with the compositions and methods provided herein. One of skill in the art can select additional components and determine suitable amounts and formulations such that the final composition functions with the desired degree of effectiveness to remove lacquer as provided herein.

The foregoing descriptions illustrate selected embodiments of the present invention and in light thereof various modifications will be suggested to one of skill in the art, all of which are in the spirit and purview of this invention.

FORMULATION EXAMPLES

A formulation of the present disclosure comprises a mixture of about 75-93% water, about 2.0-5.0% Tetrasodium Iminidisuccinate, about 0.5-4.0% Monoethanolamine, about 1.0-5.0% Sodium Silicate, about 1.5-7.0% Amphoteric surfactant, about 1.5-7.0% Amine Oxide, and about 1.5-7.0% Quaternary Amine. The formulation of the present disclosure is generally applied at a pH of between 6.0 and 8.0; however, depending upon the intended use of the product, the pH can be adjusted. The CAS number of water is 7732-18-5. The CAS number of Tetrasodium Iminidisuccinate is 144538-83-0. The CAS number of Monoethanolamine is 141-43-5. The CAS number of Sodium Silicate is 1344-09-8. The CAS number of amphoteric surfactant is 64972-19-6. The CAS number of amine oxide is 68478-65-9. The CAS number of Quaternary amine is 68610-19-5.

A specific embodiment of the formulation of the present disclosure comprises a mixture of 83.9% water, 3.0% Tetrasodium Iminidisuccinate, 1.5% Monoethanolamine. 3.0% Sodium Silicate, 3.0% Amphoteric surfactant, about 2.8% Amine Oxide, and 2.8% Quaternary Amine. The formulation of the present disclosure is applied at a pH of 12.0.

A second embodiment of this formulation substitutes CAS 144538-83-0 with CAS 6381-92-6, however, the cleaning performance of the formulation is somewhat reduced. An embodiment of this formulation substitutes CAS 1344-09-8 with CAS 6834-92-0. In a fourth embodiment of this formulation, CAS 61789-39-7 can substitute for CAS 64972-19-6. In a fifth embodiment of this formulation, CAS 71486-82-3 or 223129-76-8 can substitute for CAS 68478-65-9. In a sixth embodiment of this formulation either CAS 61791-10-4 or CAS 68478-94-4 can be substituted for CAS 68610-19-5.

What is claimed is:

1. A multi-purpose cleaning composition comprising:
   tetrasodium iminodisuccinate between 3.0 and 5.0 wt. % of the cleaning composition;
   monoethanolamine between 0.5 and 4.0 wt. % of the cleaning composition;
   sodium silicate between 1.0 and 5.0 wt. % of the cleaning composition;
   an amphoteric surfactant which is 1-Propanaminium, 3-amino-N-(carhoxymethyl)-N,N-dimethyl-, N-coco acyl derivs, chlorides, sodium salts between 1.5 and 7.0 wt. % of the cleaning composition; and,
   water.

2. The composition of claim 1, further comprising a thickening agent.

3. The composition of claim 2, where the thickening agent is between 1.5-7.0 wt. % of the cleaning composition.

4. The composition of claim 3, wherein the thickening agent is amine oxide.

5. The composition of claim 1, further comprising a quaternary amine.

6. The composition of claim 5, wherein the quaternary amine is between 1,5 and 7.0 wt. % of the cleaning composition.

7. The composition of claim 6, wherein the quaternary amine is 3-tridecyloxypropanamine chloride, ethoxylated.

8. The composition of claim 1, wherein the water is between 75 and 93 wt. % of the cleaning composition.

9. The composition of claim 1, wherein the composition is applied at a pH of between 6.0 and 8.0.

10. The multi-purpose cleaning composition according to claim 1, wherein the multi-purpose cleaning composition is environmentally benign.

* * * * *